(12) United States Patent
Sundaram (10) Patent No.: US 11,384,329 B2
(45) Date of Patent: Jul. 12, 2022

(54) PHOTOBIOREACTORS, GAS CONCENTRATORS, AND PERIODIC SURFACES

(71) Applicant: ExxonMobil Technology and Engineering Company, Annandale, NJ (US)

(72) Inventor: Narasimhan Sundaram, Annandale, NJ (US)

(73) Assignee: ExxonMobil Technology and Engineering Company, Annandale, NJ (US)

(*) Notice: Subject to any disclaimer, the term of this patent is extended or adjusted under 35 U.S.C. 154(b) by 33 days.

(21) Appl. No.: 16/891,211

(22) Filed: Jun. 3, 2020

(65) Prior Publication Data
US 2021/0087513 A1    Mar. 25, 2021

Related U.S. Application Data

(60) Provisional application No. 62/904,056, filed on Sep. 23, 2019.

(51) Int. Cl.
| C12M 3/00 | (2006.01) |
| C12M 1/00 | (2006.01) |
| C12M 1/34 | (2006.01) |

(52) U.S. Cl.
CPC ............ *C12M 29/24* (2013.01); *C12M 21/02* (2013.01); *C12M 41/16* (2013.01)

(58) Field of Classification Search
CPC .............................. C12M 21/02; C12M 29/24
See application file for complete search history.

(56) References Cited

U.S. PATENT DOCUMENTS

| 8,586,353 | B2 | 11/2013 | Woods et al. |
| 9,523,070 | B2 | 12/2016 | Erickson et al. |
| 9,790,458 | B2 | 10/2017 | Podsiadlo |
| 9,896,652 | B2 | 2/2018 | Ashley et al. |
| 10,149,422 | B2 | 12/2018 | Tippery et al. |
| 10,150,112 | B2* | 12/2018 | Wright ................... B01D 53/62 |
| 2013/0059369 | A1* | 3/2013 | Lin ......................... C12M 23/58 435/292.1 |
| 2013/0312606 | A1* | 11/2013 | Eisenberger ........... B01D 53/06 95/104 |
| 2015/0024453 | A1* | 1/2015 | Fradette ................... C12N 9/88 435/168 |
| 2017/0296961 | A1* | 10/2017 | Beaumont ................ B01J 20/20 |
| 2018/0105780 | A1* | 4/2018 | Rittman .................. C12M 41/26 |
| 2021/0093998 | A1* | 4/2021 | Kupper ................ B01D 53/053 |

* cited by examiner

*Primary Examiner* — Nathan A Bowers
(74) *Attorney, Agent, or Firm* — Kristina Okafor (57) ABSTRACT

A system for growing algae includes a gas concentrator configured to receive a first gas containing CO2 at a first concentration and discharge a second gas containing CO2 at a second concentration higher than the first concentration, and a photobioreactor containing algae in an algae slurry and fluidically coupled to the gas concentrator to receive the second gas. A recycling line extends from a gas outlet on the photobioreactor to remove a third gas from the photobioreactor for future use in the photobioreactor.

7 Claims, 6 Drawing Sheets

PHOTOBIOREACTORS, GAS CONCENTRATORS, AND PERIODIC SURFACES

CROSS-REFERENCE TO RELATED APPLICATIONS

This application claims priority to U.S. Provisional Application No. 62/904,056 filed Sep. 23, 2019, which is herein incorporated by reference in its entirety.

BACKGROUND OF THE INVENTION

Concerns about climate change, carbon dioxide ($CO_2$) emissions, and depletion of subterranean oil and gas resources have led to widespread interest in the production of biofuels from algae and microalgae. As used herein, the term "biofuel" refers to any type of fuel produced from algae, and the term "algae" will include microalgae, unless explicitly distinguished.

As compared to some other plant-based biofuel feedstocks, algae have higher $CO_2$ fixation efficiencies and growth rates, and growing algae can efficiently utilize wastewater and industrial gases as nutrient sources. The biomass of algae stores increasing quantities of lipids as it grows. Methods for harvesting and utilizing algae involve extracting and converting their stored lipids and carbohydrates into renewable biofuels, such as diesel and jet fuel, or into other hydrocarbons, as examples.

Algae biomass is generally grown in a water slurry contained in a bioreactor system. Algae bioreactors are sometimes referred to as "photobioreactors" since they utilize a light source to cultivate algae, which are photoautotrophic organisms or organisms that can survive, grow, and reproduce with energy derived entirely from the sun through the process of photosynthesis. Photosynthesis, aided by other cellular biochemical processes, is essentially a carbon recycling process through which inorganic $CO_2$ is absorbed and combined with solar energy, nutrients, and water to synthesize carbohydrates, lipids, and other compounds necessary to algae life. In addition to production of lipids and carbohydrates for biofuel production, the benefits of growing and harvesting algae includes utilization of $CO_2$ and production of oxygen.

The $CO_2$ used for algae growth may come from any suitable source, including atmospheric air, flue gas/exhaust streams from a combustion process, or a storage location including tanks or geological formations, as examples. In some locations, options are limited primarily or exclusively to atmospheric air or another relatively low-concentration source of $CO_2$. In these locations and others, equipment and methods that provide improvements to the delivery of $CO_2$ for algae growth would be desirable.

SUMMARY

The present disclosure is related to growing algae for biofuel production and, more particularly, to delivering concentrated gas for algae growth and to structures to enhance gas concentrators or photobioreactors.

In some embodiments, a system for growing algae includes a gas concentrator configured to receive a first gas containing CO2 at a first concentration and discharge a second gas containing CO2 at a second concentration higher than the first concentration, a photobioreactor containing algae in an algae slurry and fluidically coupled to the gas concentrator to receive the second gas, and a recycling line extending from a gas outlet on the photobioreactor to remove a third gas from the photobioreactor for future use in the photobioreactor.

In some embodiments, a method for growing algae is disclosed herein and includes receiving a first gas containing CO2 of a first concentration into a gas concentrator, discharging a second gas containing CO2 of a higher, second concentration from the gas concentrator, delivering the second gas to a photobioreactor containing algae in an algae slurry, wherein the gas concentrator is fluidically coupled to the photobioreactor, discharging a third gas from the photobioreactor, and recycling at least a portion of the third gas back to the photobioreactor.

In one or more additional embodiments, a gas concentrator is disclosed herein and includes a periodic structure comprising a first, periodic surface and a second surface, an adsorbent material disposed adjacent or on the first, periodic surface to absorb CO2 from a mixture of gases, a first flow path that is at least partially defined by the first, periodic surface and the adsorbent material, and a second flow path that includes the second surface.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure is related to growing algae for biofuel production and, more particularly, to delivering concentrated gas for algae growth and to structures configured to enhance operation of gas concentrators or photobioreactors.

Figure 1:
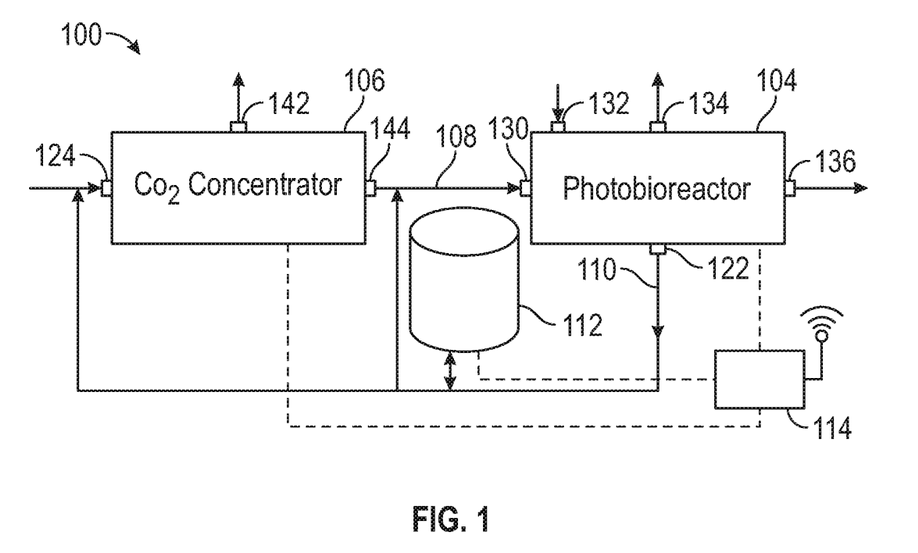
FIG. 1 is a schematic diagram of an example system for growing algae, according to one or more embodiments of the present disclosure.

FIG. 1 is a schematic diagram of an example system 100 for growing algae, according to one or more embodiments of the present disclosure. As illustrated, the system 100 includes a photobioreactor (PBR) 104 and a gas concentrator 106 fluidically coupled by a transfer line 108. The PBR 104 may be any type of bioreactor configured for the cultivation, growth, and harvesting of algae from an algae slurry contained within the PBR 104. Examples of the PBR 104 include, but are not limited to, an open pond, a closed pond, an open reactor vessel, and a closed reactor vessel. Though not shown, the system 100 may also include any of the following: suitable valving, a water supply, and other equipment to support algae growth and harvesting.

As used herein, the term "algae slurry," and grammatical variants thereof, refers to a flowable liquid mixture comprising water, algae cells, and nutrients. The algae cells may alternately referred to as "algae" or "algae biomass." As used herein, the term "gas" refers to a single gas or a mixture of gases.

As illustrated, the system 100 may further include a recycling line 110 and a gas storage tank 112. The recycling line 110 fluidically couples a gas port 122 on the PBR 104 to an inlet 124 of the gas concentrator 106 or to the transfer line 108. In some embodiments, the recycling line 110 may include a check valve to ensure fluid may exit gas port 122 but may not enter it. Some embodiments of the system 100 include multiple gas concentrators 106 fluidically coupled to one or more photobioreactors 104. Some of the gas concentrators 106 may be disposed adjacent the one or more PBRs 104 to reduce piping or pressure drop or to improve utilization of available space, as examples.

The storage tank 112 is in fluid communication with the gas concentrator 106 and the PBR 104 to collect, hold, and release a gas, such as one or more gases containing carbon dioxide ($CO_2$). In this example, the recycling line 110 provides fluid communication between the storage tank 112 and the gas concentrator 106 and the PBR 104. In some embodiments, the storage tank 112 may receive gas discharged from the gas concentrator 106. In other embodiments, or in addition thereto, the storage tank 112 may receive gas discharged from the PBR 104. The recycling line 110 may be configured to selectively feed discharged gases back to either the gas concentrator 106 or the PBR 104, and the storage tank 112 may be tapped as needed. Thus, at various stages of operation, the storage tank 112 may receive and discharge one or more gases containing carbon dioxide ($CO_2$), which may be ultimately fed back into the PBR 104. In some embodiments, the storage tank 112 may be located adjacent the gas concentrator 106 or the PBR 104 to reduce piping, which may reduce pressure drop (operational costs) and capital costs, or to improve utilization of available space (e.g., land, plant floor area), as examples.

As illustrated in FIG. 1, the PBR 104 includes an inlet 130 fluidically coupled to transfer line 108 to receive a gas containing $CO_2$, an inlet 132 to receive water, nutrients, or algae seed material to make the algae slurry, the gas port 122 coupled to recycling line 110, an outlet 134 to discharge a byproduct gas including oxygen ($O_2$) produced and released by algae, and a product outlet 136 to discharge algae biomass, which may be in a slurry. Other equipment downstream of the product outlet 136 may separate, filter, or otherwise process the discharged algae.

The gas concentrator 106 includes the inlet 124 to receive a first gas, an outlet 142 to discharge unwanted a gas, and an outlet 144 fluidically coupled to the transfer line 108 to discharge a second gas containing $CO_2$ at a higher concentration than is present in the first gas. The first gas may come from any suitable source, including atmospheric air, flue gas/exhaust streams from a combustion process, or a storage location including tanks or geological formations, as examples. The gas concentrator 106 may operate using a process selected from a group that includes pressure swing adsorption, vacuum swing adsorption, voltage swing adsorption, temperature swing adsorption, displacement desorption, and any combination thereof, as examples.

The system 100 may further include a control system 114 used to operate the system 100. The control system 114 may include a controller, instrumentation, and machine-readable code that causes operation of the controller. In example operation, the control system 114 may be configured or otherwise programmed to monitor or control the flow of fluids through the various inlets, outlets, and lines of the system 100, and to maintain and adjust fluid levels within the PBR 104, as examples.

During an example first stage of operation, the PBR 104 contains an algae slurry for the growth and cultivation of algae. The gas concentrator 106 receives through the inlet 124 a first gas containing $CO_2$ at a first concentration, discharges through the outlet 142 unwanted gas, and discharges to the transfer line 108 the second gas, which contains $CO_2$ at a second concentration higher than the first concentration. The transfer line 108 transfers the second gas containing $CO_2$ to the PBR 104. During a growth period, the algae in the PBR 104 absorbs $CO_2$ from the second gas, which may be bubbled or sparged through the algae slurry, and the algae produces and releases oxygen. A third gas (e.g., a mixture of gases) may accumulate in the PBR 104. During the first stage of operation, the third gas includes the produced oxygen and, potentially, a residual portion of the second gas that entered the PBR 104, which may include nitrogen, oxygen, or $CO_2$, as examples. During the first stage, the third gas may be discharged from the PBR 104 though outlet 134 as a byproduct gas.

During a second stage of operation for the system 100, the third gas include $CO_2$ is taken from the PBR 104 and is directed through the recycling line 110. The third gas that enters the recycling line 110 from the PBR 104 may be sent to the gas concentrator 106, the gas storage tank 112, the transfer line 108, or any combination of these destinations. Ultimately, the third gas or some of its $CO_2$, may be returned to the PBR 104. For example, the third gas may be combined into the second gas at the transfer line 108 and delivered to the PBR 104 during a subsequent occurrence of the first stage of operation. Some embodiments or operational modes of the system 100 may exclude the second stage of operation.

During the second stage, a flow of gas from the transfer line 108 to the PBR 104 may be shut-off. The execution of the various stages of operation of the system 100 may be governed by the control system 114, which may allow or disallow fluid communication between the transfer line 108 and the PBR 104 or between the PBR 104 and recycling line 110. The control system 114 may be configured to direct the third gas coming from the PBR 104 to the recycling line 110, the transfer line 108, the gas concentrator 106, the gas storage tank 112, or any combination of these destinations. In some cases, the control system 114 may be configured to direct the third gas back to the PBR 104. This recycling of the third gas may occur during the current second stage of operation, during a future first stage, or during a future second stage. In this manner, the third gas may be recycled through the system 100. In some embodiments, the operational stages (e.g. time periods) of PBR 104, including the recycling of gas through line 110, may be, alternatively, controlled manually.

The algae in the PBR 104 may release $CO_2$ during a portion of its life cycle, such as when photosynthesis in the algae ceases. The released $CO_2$ may have been produced by the algae or may have been temporarily held by the algae. The released $CO_2$, becomes a portion or constituent of the third gas within the PBR 104. During this time frame, the third gas is anticipated to include a residual portion of the second gas that entered the PBR 104 through the transfer line 108, in addition to the newly generated/released $CO_2$. Some released $O_2$ may also be present. Thus, the third gas is anticipated to have a composition that varies through the different stages of operation of the system 100; likewise, the composition of the second gas that enters PBR 104 is anticipated to vary due to recycling of the third gas into gas concentrator 106 or transfer line 108. The algae may release $CO_2$ periodically, such as during a night or during other periods of low light or when photosynthesis ceases. The control system 114 may include sensors to monitor, detect, or estimate time periods during which the algae is or may be releasing $CO_2$. Control system 114 may implement the second stage of operation during or subsequent to a period when it is determined or estimated that the algae is releasing $CO_2$.

Figure 2:
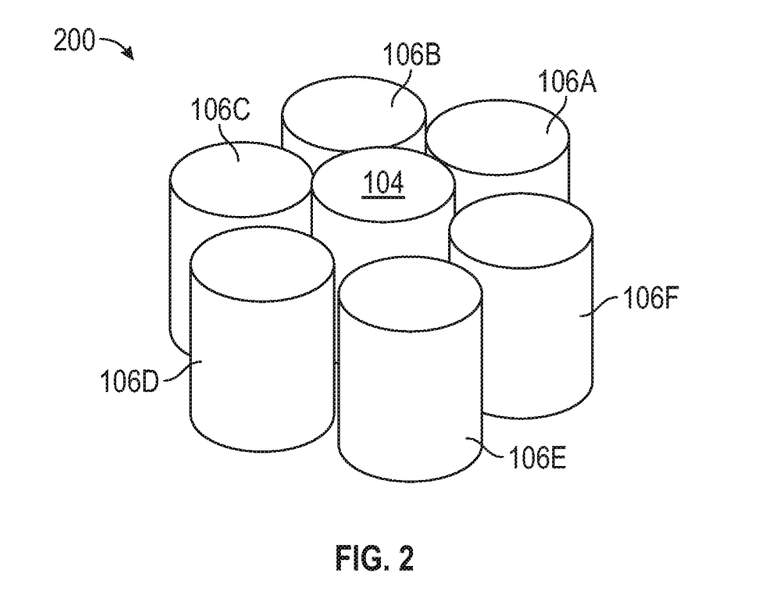
FIG. 2 illustrates another example system for growing algae, according to one or more embodiments of the present disclosure.

FIG. 2 presents another example system 200 for growing algae, according to one or more additional embodiments of the present disclosure. System 200 includes the PBR 104 and a plurality of gas concentrators 106 located (i.e., disposed) in close proximity to the PBR 104. In this example, the PBR 104 and the gas concentrators, shown as gas concentrators 106A-106F. The six gas concentrators 106A-F are shown with cylindrical bodies having circular foot prints and arranged around PBR 104 and adjacent to it. Other embodiments of the system 200 may include more or fewer gas concentrators located around or adjacent the PBR 104, based on the shapes and the relative sizes of these different components or based on another design criterion, such as the efficiency of the selected type of gas concentrator(s). The tight arrangement of the system 200, as shown, may result in reduced piping or pressure drop or improved utilization of available space, or another benefit.

The system 200 is an example embodiment of the system 100 of FIG. 1. In general, unless specifically described as being different, the configurations and operations, including the potential variations described for the system 100 of FIG. 1 and its various components, are applicable to the system 200 and its corresponding components, respectively. For example, some or all of the fluidic couplings shown if FIG. 1 are applicable to one or more portions of the system 200 of FIG. 2. The gas concentrators 106A-F may be selected so that they all use the same process, or one or more may use a different process than one or more of the other gas concentrators. Examples of processes for gas concentrator were described above with reference to FIG. 1.

In some embodiments, the system 200 may include one or more storage tanks (not shown) coupled to or adjacent to one or more of the gas concentrators 106A-G or the PBR 104. The storage tank(s) may be similar to the storage tank 112 of FIG. 1, and may be used to store $CO_2$ for recycling back through the system 200 at predetermined intervals or otherwise as needed. In some embodiments, alternating gas concentrators, for example gas concentrators 106B, D, F, may be replaced by a storage tank to achieve the tight arrangement shown in FIG. 2, while having both gas concentrator and storage tank immediately adjacent the PBR 104. Alternatively, or in addition thereto, the storage tanks and gas concentrators may be stacked. In some embodiments, the system 200 may include multiple systems 200 arranged in series or parallel. Moreover, in some embodiments based on the system 200, multiple photobioreactors 104 may share one or more gas concentrators, or one or more storage tanks in a tight arrangement.

Figure 3:
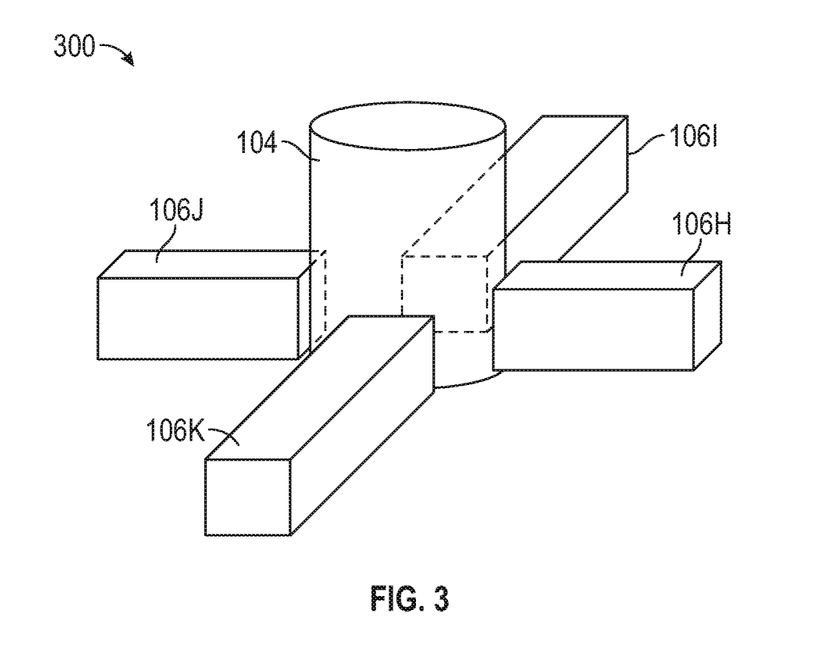
FIG. 3 illustrates still another example system for growing algae, according to one or more embodiments of the present disclosure.

FIG. 3 presents still another example system 300 for growing algae, according to one or more additional embodiments of the present disclosure. System 300 includes the PBR 104 and a plurality of gas concentrators, shown as gas concentrators 106H-106K, arranged in close proximity to the PBR 104. In this example, the PBR 104 and the gas concentrators are shown with rectangular bodies having rectangular foot prints, and the system 300 is shown with four gas concentrators 106H-K located around PBR 104 and extending lengthwise away from the PBR 104. Other orientations of one or more of the concentrators 106H-K with respect to the PBR 104 are possible, without departing from the scope of the disclosure. Other embodiments of the system 300 may include more or fewer gas concentrators 106H-K located around or adjacent the PBR 104, based on the shapes and the relative sizes of these different components or based on another design criterion, such as the efficiency of the selected type of gas concentrator(s). The tight arrangement of the system 300, as shown, may result in reduced piping or pressure drop or improved utilization of available space, or another benefit.

The system 300 is an example embodiment of the system 100 of FIG. 1. In general, unless specifically described as being different, the configurations and operations, including the potential variations, described for the system 100 of FIG. 1 and its various components, are applicable to the system 300 and its corresponding components, respectively. For example, some or all of the fluidic couplings shown if FIG. 1 are applicable to one or more portions of the system 300 of FIG. 3. The gas concentrators 106H-K may be selected so that they all use the same process, or one or more may use a different process than one or more of the other gas concentrators. Examples of processes for gas concentrators were described above with reference to FIG. 1.

In some embodiments, the system 300 may include one or more storage tanks (not shown) coupled to or adjacent to one or more of the gas concentrators 106H-K or the PBR 104. In some embodiments, alternating gas concentrators, for example the gas concentrators 106I, K, may be each replaced by a storage tank (e.g., the storage tank 112 of FIG. 1) to achieve the tight arrangement shown in FIG. 3, while having both gas concentrator and storage tank immediately adjacent the PBR 104, or the storage tanks and the gas concentrators 106H-K may be stacked. In some embodiments, the system 300 may include two or more systems 300 arranged in series or parallel. In some embodiments based on the system 300, multiple photobioreactors 104 share one or more gas concentrators 106H-K or one or more storage tanks in a tight arrangement.

Figure 4:
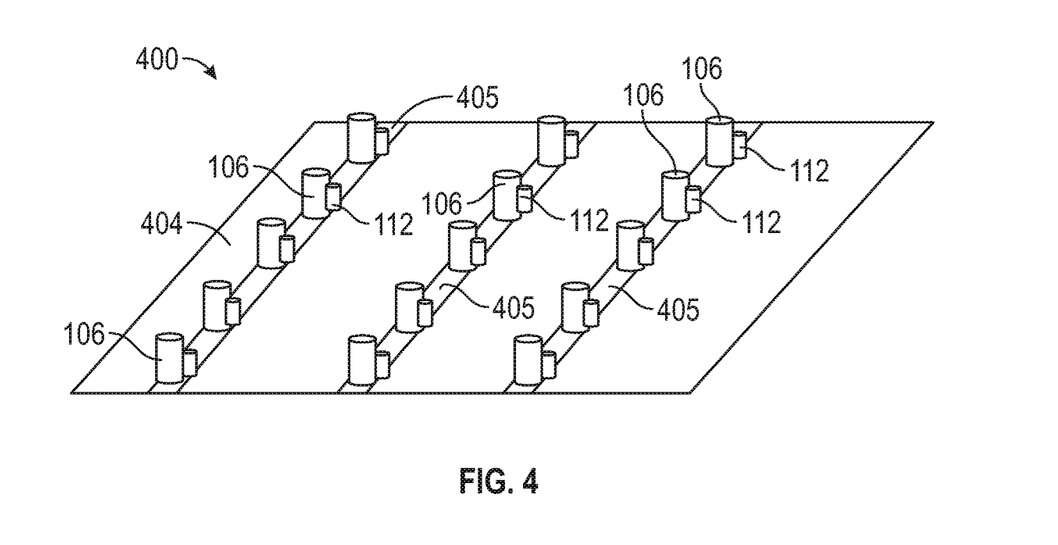
FIG. 4 illustrates an example system for growing algae in a pond, according to one or more embodiments of the present disclosure.

FIG. 4 illustrates another example system 400 for growing algae in a pond 404, according to one or more embodiments of the present disclosure. The pond 404 may be an open pond or a closed pond and may include a covering in various embodiments. Although the pond 404 is represented as being rectangular as viewed from above, in other embodiments, the pond 404 may include any suitable shape. As illustrated, the pond 404 may include a plurality of gas concentrators 106 paired with a plurality of storage tanks 112 and spaced apart on one or more support structures or islands 405 extending over a portion of the pond 404 or otherwise located in the pond 404. This distributed arrangement of the system 400 may result in reduced piping or pressure drop for fluid flows between pond 404, the gas concentrators 106, and the adjacent storage tanks 112, and may also improve utilization of available space.

The system 400 is an example embodiment of the system 100 of FIG. 1. In general, unless specifically described as being different, the configurations and operations, including the potential variations, described for the system 100 of FIG. 1 and its various components, are applicable to the system 400 and its corresponding components, respectively. For example, some or all of the fluidic couplings shown in FIG. 1 are applicable to one or more portions of the system 400 of FIG. 4. As another example, in some embodiments of the system 400, the gas concentrators 106 or storage tanks 112 may collect $CO_2$ released by algae in pond 404 during a portion of its life cycle and may recycle it back to pond 404 during another time period. In some embodiments, for example, this can be done with a collection system configured to outgas the $CO_2$ (e.g., reduce its solubility) by mild changes in temperature of the fluid (water). This can be performed, for instance, by passing the water thru a collection pipe that is suitably heated and has provisions to allow the gas collected to be conveyed outside the pond 404. The water can be moved using an impeller or similar device.

The gas concentrators 106 of FIG. 4 may be selected so that they all use the same process, or one or more may use a different process than one or more of the other gas concentrators. Examples of processes for gas concentrators were described above with reference to FIG. 1. Some pairs that include a gas concentrator 106 fluidically coupled to an adjacent storage tank 112 may be fluidically coupled other pairs to share supply lines or transfer lines.

Figure 5:
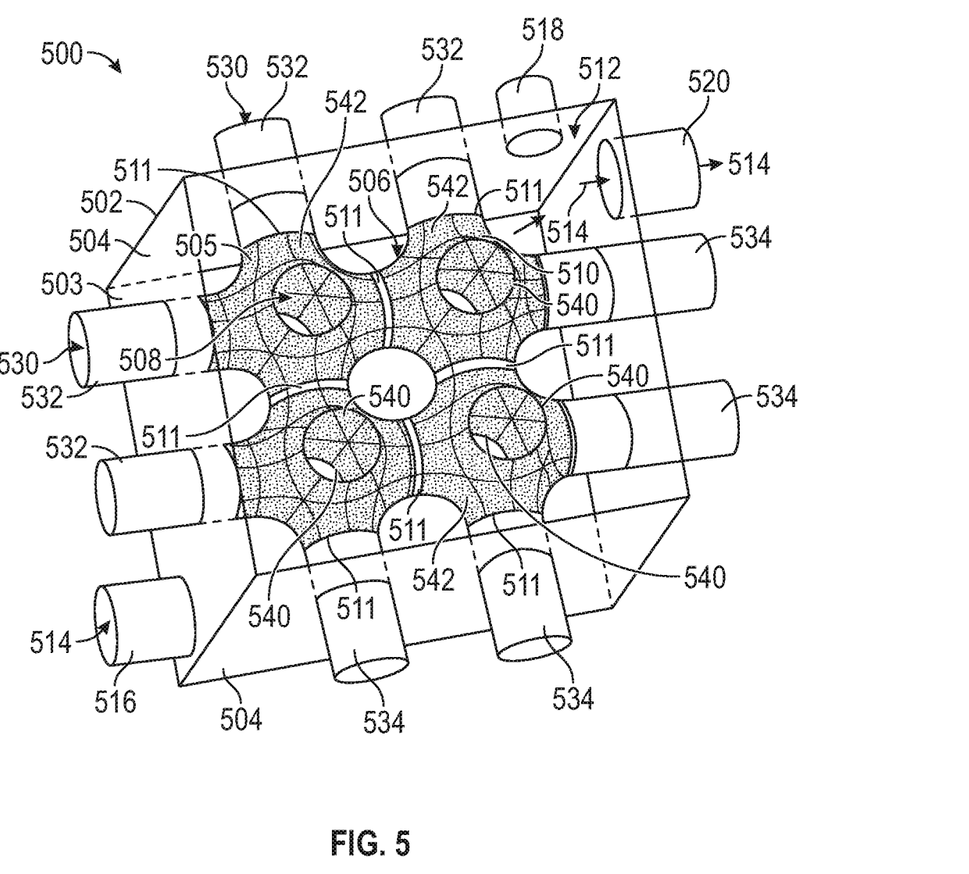
FIG. 5 illustrates an example gas concentrator, according to one or more embodiments of the present disclosure.

FIG. 5 illustrates an example gas concentrator 500, according to one or more embodiments of the present disclosure. The gas concentrator 500 may be the same as or similar to any of the gas concentrators 106 used in the systems 100, 200, 300, 400 described herein. As illustrated, the gas concentrator 500 includes a body or shell 502 that contains one or more periodic structures 505, which includes a first periodic surface 506 and a second periodic surface 508 generally facing opposite the first periodic surface 506. An adsorbent material 510 may be disposed adjacent or on the periodic surfaces 506, and one or more mechanisms 511 may be included on the periodic structure 505 to cause movement of the periodic structure 505.

In this example, the first periodic surface 506 is an outer surface for the periodic structure 505, and the second periodic surface 508 is an inner surface for the periodic structure 505 and is also periodic. The outer, periodic surface 506 and the inner, periodic, second surface 508 define the thin-wall shell 502 of the periodic structure 505. In various embodiments, the adsorbent material is attached to the periodic surface 506, coats the periodic surface 506, or is incorporated into pellets or monoliths, equivalently, granules located in an inner volume 512 of the shell 502, potentially contacting the periodic surface 506. The adsorbent material 510 is capable of preferentially absorbing $CO_2$ from a mixture of gases. The adsorbent material 510 may include a metal organic framework (MOF), amine-appended MOF with a Type V isotherm for $CO_2$, an amine appended MOF with a Type 1 isotherm for $CO_2$, a metal impregnated microporous silicate, metal impregnated alkalized alumina, mixed-metal oxides, hydrotalcites, treated activated carbons including metal doped carbons, and any combination thereof, as examples. The gas concentrator 500 may operate using a process selected from a group that includes pressure swing adsorption, vacuum swing adsorption, voltage swing adsorption, temperature swing adsorption, displacement desorption, and any combination thereof, as examples.

In FIG. 5, the shell 502 is depicted with a bottom wall 503 and side walls 504. An upper wall or surface is removed to expose the inner volume 512 of the shell 502. A first flow path 514 through gas concentrator 500 includes an inlet 516, the inner volume 512 of shell 502, an outlet 518 to discharge unwanted a gas, and an outlet 520 to release a product gas that may contain $CO_2$ at an increased concentration as compared to a gas that entered at inlet 516. The inner volume 512 of the shell 502 is defined in part by the periodic surface 506 and the adsorbent material 510. Some embodiments may include multiple inlets 516 or multiple outlets 520.

A second flow path 530 through the gas concentrator 500 includes the second surface 508 of periodic structure 505, one or more inlets 532, and one or more outlets 534 fluidically coupled to second surface 508. In various embodiments, multiple inlets 532 may be merged or routed to fewer inlets, perhaps a single inlet, by a manifold located within or outside shell 520, and the multiple outlets 534 may be similarly merged or routed. Other quantities, relative quantities, or arrangements of the inlets 532 and outlets 534 are possible. Due to the multiple inlets 532 and outlets 534 and due to the multiple, intersecting passageways defined by the second surface 508, the second flow path 530 includes multiple intersecting routes for a fluid to travel inside periodic structure 505. The second flow path 530 may be fluidically separated from the first flow path 514. The thin-wall, shell-like configuration of the periodic structure 505 may augment efficient heat transfer between a fluid in the first flow path 514 and another fluid in the second flow path 530.

The periodic structure 505 includes multiple, repeating patterns or smaller periodic structures 542, which are incremental portions, possibly "building blocks," of the larger periodic structure 505. Each periodic structure 542 defines a portion of periodic surface 506 and a portion of a second surface 508. FIG. 5 shows four of the periodic structures 542 forming a single layer that extends generally parallel to the bottom 503 of the shell 502. Various embodiments may include more or fewer of the periodic structures 542 in a layer. The periodic structure 505 is depicted with the apertures 540 that are open in directions generally perpendicular to bottom 503. Although FIG. 5 shows a single layer of the periodic structure 505, apertures 540 accommodate additional layers of periodic structure 505 that may be placed generally parallel to the depicted layer and may be fluidically coupled through apertures 540. Alternatively, some embodiments may include only one layer of the periodic structure 505, and the apertures 540 are either closed or non-existent. Thus, the gas concentrator 500 includes a plurality of periodic structures (e.g., the structures 542 or the layers of adjoined structures 542), and the first flow path 514 includes the periodic surfaces of the plurality of periodic structures, and the second flow path 530 includes the second surfaces of the plurality of periodic structures.

In the example of FIG. 5, the plurality of the mechanisms 511 are selected and positioned to cause movement of periodic structure 505. The mechanisms 511 may be coupled to or integrated into the outer, periodic surface 506, the inner, second surface 508 or may be embedded in the structure of periodic structure 505 in any combination. In FIG. 5, the mechanisms 511 are located at regions of minimal diameter on periodic structure 505 and extend circumferentially around, but other positions and other arrangements may be utilized in some embodiments. The movement of periodic structure 505 caused by mechanism 511 may be vibration, expansion, contraction, or a combination of these modes of movement, as examples. The contractions and expansions may be radially-directed, axially-directed, or a combination of these movements in some embodiments. The mechanisms 511 may induce peristaltic motion in the periodic structure 505 and its periodic surface 506, 508. The movement of periodic structure 505 may promote the movement of the heat transfer fluid through flow path 530 of the gas concentrator. The operation of mechanisms 511 may be governed by a controller, such as the control system 114 of FIG. 1.

In some embodiments, a first, second, and third mechanism 511 are spaced apart from each other and are configured to produce a first, second, and third periodic cycles of contractions and expansions, respectively. In some examples, the second periodic cycle of the contractions and expansions is out-of-phase with the first periodic cycle of the contractions and expansions. Also, the third periodic cycle of the contractions and expansions is out-of-phase with the second periodic cycle of the contractions and expansions. In some examples, the out-of-phase cycles of the contractions and expansions (e.g., any two of the mentioned periodic cycles or the first, second, and third periodic cycles working together) cause the peristaltic motion in the periodic structure 505 and its periodic surface 506, 508.

Example operation of gas concentrator 500 may include receiving a first gas into the first flow path 514, obtaining a second gas from the first flow path 514 via the outlet 520, and passing a heat transfer fluid through the second flow path 530 to provide cooling to the periodic structure 505 and the adsorbent material 510. The heat transfer fluid may be a liquid or a gas. The first gas may come from any suitable source, including atmospheric air, flue gas/exhaust streams from a combustion process, or a storage location including tanks or geological formations, as examples. The second gas contains $CO_2$ at a higher concentration than was present in the first gas. Obtaining the second gas from the first flow path 514 may include one or more of the following steps: absorbing $CO_2$ into the adsorbent 510, opening the outlet 518 to release non-absorbed portions of the first gas, closing the outlet 518, and opening outlet 520 to release the second gas to a downstream storage location or process, a process such as a PBR 104 of FIG. 1. When activated, the mechanisms 511 may cause beneficial agitation in the fluid in the first flow path 514, the fluid in the second flow path 530, or in both fluids. The motions of the mechanisms 511 may be synchronized to produce the first, second, and third, periodic cycles of the contractions and expansions in the periodic structure 505 to induce movement in one or more of those fluids. In some embodiments, the motions of the mechanisms 511 may be synchronized to induce a peristaltic movement in the periodic structure 505 to induce movement in the fluid in the first flow path 514, the fluid in the second flow path 530, or in both fluids. Other operations of the apparatus 500 may pass the heat transfer fluid through the second flow path 530 to provide heating to the periodic structure 505 and to the fluid in first flow path 514.

Figure 6A:
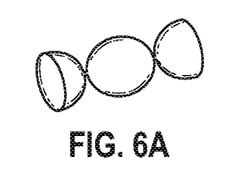
FIGS. 6A-6C depict examples of singly periodic structures of which the gas concentrator of FIG. 5 may be formed or may include.
Figure 6B:
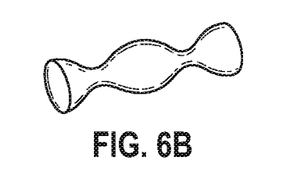
Figure 6C:
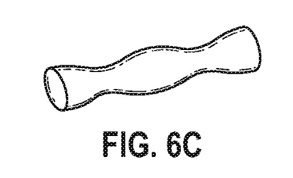
Figure 7A:
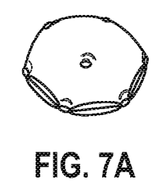
FIGS. 7A-7E depict examples of doubly periodic structures of which the gas concentrator of FIG. 5 may be formed or may include.
Figure 7B:
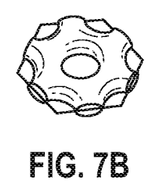
Figure 7C:
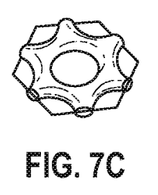
Figure 7D:
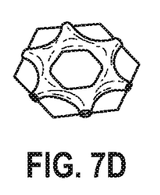
Figure 7E:
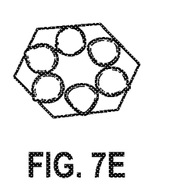
Figure 8A:
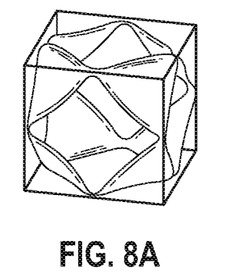
FIGS. 8A-8E depict examples of triply periodic structures of which the gas concentrator of FIG. 5 may be formed or may include.
Figure 8B:
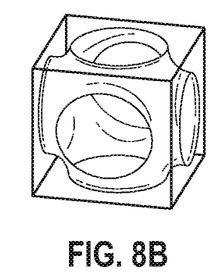
Figure 8C:
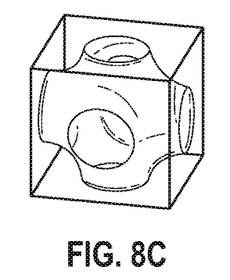
Figure 8D:
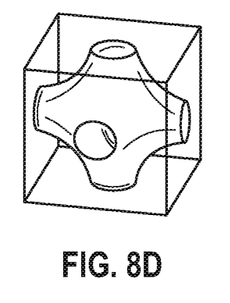
Figure 8E:
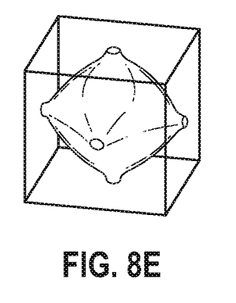

FIGS. 6A-6C depict examples of singly periodic structures of which the gas concentrator 500 of FIG. 5 may be formed or may include. As illustrated, the singly periodic structures can periodically transition between a sphere or bulbous section and a cylinder. Typically, a singly periodic structure exhibits a periodicity along a single axis. This periodicity in the surface can be, for example, a regular undulation or curvature that repeats exactly. For the purposes of gas concentrators, the singly periodic surface is a surface that includes curvature in addition to the curvature of a cylindrical surface.

FIGS. 7A-7EF depict examples of doubly periodic structures of which the gas concentrator 500 of FIG. 5 may be formed or may include, and FIGS. 8A-8E depict examples of triply periodic structures of which the gas concentrator 500 of FIG. 5 may be formed or may include. Doubly periodic structures approach two families of orthogonal planes, and triply periodic structures are minimal structures in three dimensions in $R^3$ that is invariant under a rank-3 lattice of translations. Triply periodic structures have the symmetries of a crystallographic group, such as cubic, tetragonal, rhombohedral, and orthorhombic symmetries. Doubly and triply periodic surfaces possess additional axes of periodicity (i.e., in the Y and Z directions), which are therefore capable of introducing additional surface features. In addition, all such periodic surfaces can be mass-produced efficiently with modern 3D printing techniques. One advantage of triply periodic to surfaces is their ability to provide minimal surfaces, which minimize the volume of material for the surface provided. This occurs in a variety of examples in nature, including butterfly wings, which have remarkable resilience yet are extremely lightweight. This feature is advantageous for increasing photobioreactor wall strength while using only minimal amount of material, which latter also maintains light absorption and control.

Figure 9:
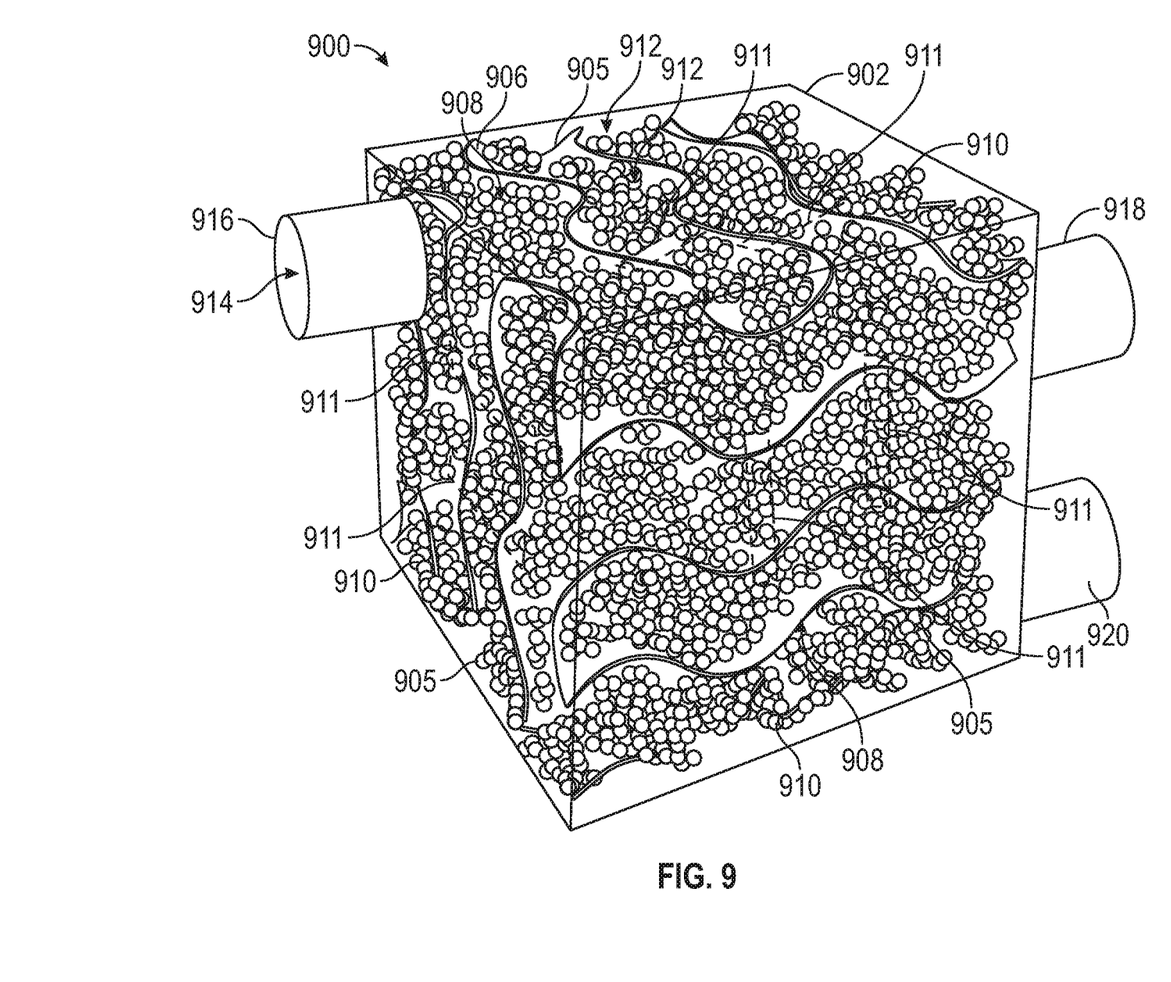
FIG. 9 illustrates another example gas concentrator, according to one or more embodiments of the present disclosure.

FIG. 9 illustrates another example gas concentrator 900, according to one or more additional embodiments of the present disclosure. The gas concentrator 900 may be the same as or similar to any of the gas concentrators 106 used in the systems 100, 200, 300, 400 described herein. As illustrated, the gas concentrator 900 includes a body or shell 902 that contains one or more periodic structures 905, an adsorbent material 910 disposed adjacent or on the periodic structures 905 within an inner volume 912 of the shell 902, and one or more mechanisms 911 (shown as dashed boxes) to cause movement of the periodic structures 905. In some illustrative examples, actuation of the mechanisms 911 can consist of mechanical perturbations delivered from the boundaries of the periodic structures 905. In one such case, the outer edges of the surfaces of the periodic structures 905 can be wrapped around a mandrel, which can be wound or unwound to generate motion throughout the corresponding surface. Similar mandrels can be used at the other boundaries. In other embodiments, however, perturbations can alternatively be possible and generated using ultrasonic means.

The present embodiment includes a plurality of periodic structures 905, each formed as a smoothly curved sheet that includes a first, periodic surface 906 and a second, periodic surface 908 generally facing opposite the first surface 906. The adsorbent material 910 may be configured as pellets or, equivalently, granules distributed among the periodic structures 905 and associated surfaces 906, 908. Considering any of the various periodic structures 905, a portion of the granules is located adjacent the first periodic surface 906 and another portion of the granules located adjacent the second periodic surface 908. In various embodiments, the adsorbent material is attached to or coats the periodic surface 906 or the second surface 908 in place of or in addition to the granules. The adsorbent material 910 is capable of preferentially absorbing $CO_2$ from a mixture of gases. The adsorbent material 910 may include a metal organic framework (MOF), amine-appended MOF with a Type V isotherm for $CO_2$, an amine appended MOF with a Type 1 isotherm for $CO_2$, a metal impregnated microporous silicate, metal impregnated alkalized alumina, mixed-metal oxides, hydrotalcites, treated activated carbons including metal doped carbons, and any combination thereof, as examples. The gas concentrator 900 may operate using a process selected from a group that includes pressure swing adsorption, vacuum swing adsorption, voltage swing adsorption, temperature swing adsorption, displacement desorption, and any combination thereof, as examples.

The shell 902 is depicted with an inlet 916, a first outlet 918, and a second outlet 920. A flow path 914 through the gas concentrator 900 is defined by the inlet 916, the inner volume 912, the periodic surfaces 906, the second surfaces 908, the outlet 918, and the second outlet 920. The granular adsorbent material 910 is contained in flow path 914. Shell 902 and the configuration of periodic structures 905 perform as a manifold to allow a fluid entering inlet 916 to be distributed among the various passageways between the several periodic structures 905 and surfaces 906, 908. The arrangements or orientations of the inlet 916 and the outlets 918, 920 may be different than are shown, and some embodiments, may include additional inlets or outlets. Some other embodiments based on gas concentrator 900 include multiple, fluidically separated flow paths in place of the combined flow path 914 and a separate inlet and outlet are provided for each flow path, similar to the configuration of FIG. 5, to keep a first or supply gas and a concentrated second gas separate from a heat transfer fluid.

The example of FIG. 9 includes a plurality of the mechanisms 911 that are selected and positioned to cause movement of periodic structure 905. The mechanisms 911 may be coupled or integrated into one or more of the periodic surfaces 906, one or more of the second surfaces 908, may be imbedded in the structure of the periodic structure 905, or may be attached to or integrated with shell 902, alone or in any feasible combination. In FIG. 9, the mechanisms 911 are located at various boundaries of the surfaces 906, 908 and, as briefly mentioned above, can consist of mechanically operated or motorized mandrels on which edges of the periodic surfaces 906, 908 are wrapped. The mandrels at one boundary can then be mechanically wound or unwound to generate the motion, operating desirably in unison with corresponding mandrels on the adjacent boundary 906, 908. In some cases, the mandrels can also be embedded at regular intervals inside the reactor 900 but accessible from the boundaries for the purposes of motorized winding or unwinding. As will be appreciated, however, other positions and other arrangements may be utilized for the mechanisms 911, without departing from the scope of the disclosure.

The movement of the periodic structure 905 caused by one or more of the mechanisms 911 may be vibration, expansion, contraction, or a combination of these modes of movement, as examples. The contractions and expansions may be radially-directed, axially-directed, or a combination of these movements in some embodiments. The operation of the mechanisms 911 may be governed by a controller, such as the control system 114 of FIG. 1.

In some embodiments, a first, second, and third mechanism 911 are spaced apart from each other and are configured to produce a first, second, and third periodic cycles of contractions and expansions, respectively. In some examples, the second periodic cycle of the contractions and expansions is out-of-phase with the first periodic cycle of the contractions and expansions. Also, the third periodic cycle of the contractions and expansions is out-of-phase with the second periodic cycle of the contractions and expansions. In some examples, the out-of-phase cycles of the contractions and expansions (e.g., any two of the mentioned periodic cycles or the first, second, and third periodic cycles working together) cause the peristaltic motion in the periodic structure 905 and its periodic surfaces 906, 908.

Example operation of the gas concentrator 900 may include receiving the first gas into the flow path 914, obtaining the second gas from the flow path 914 via the second outlet 920, and may also include passing a heat transfer fluid through the same flow path 914 to provide cooling to the periodic structure 905 and the adsorbent material 910. Both fluids would contact the absorbent material 910. The heat transfer fluid may be a liquid or a gas and the operation of the concentrator 900 may involve two-phase flow. Thus, as configured, the gas concentrator 900 provides direct contact heat transfer between a cooling fluid and the absorbent material 910 and may provide direct contact heat transfer between the cooling fluid and the first and second gases. The flow of the first gas and the flow of heat transfer fluid may be alternated or pulsed, and the outlet 918 may be closed when heat transfer fluid passes through the gas concentrator 900. The first gas may come from any suitable source, including atmospheric air, flue gas/exhaust streams from a combustion process, or a storage location including tanks or geological formations, as examples.

The second gas includes $CO_2$ at a higher concentration than was present in the first gas. Obtaining the second gas from the flow path 914 may include one or more of the following steps: absorbing $CO_2$ into the adsorbent 910, opening the outlet 918 to release non-absorbed portions of the first gas, closing the outlet 918, and opening second outlet 920 to release the second gas to a downstream storage location or a process, such as the PBR 104 of FIG. 1.

When activated, the mechanisms 911 may cause beneficial agitation or movement in one or both of the fluids in the flow path 914. For example, the motions of the mechanisms 911 may be synchronized to produce the first, second, and third, periodic cycles of the contractions and expansions in the periodic structure 905 to induce movement in one or more of those fluids. The motions of the mechanisms 911 may be synchronized to induce a peristaltic movement in the periodic structure 905 to induce movement in one or both of the fluids in the flow path 914. Other operations of the apparatus 900 may pass a heat transfer fluid through the flow path 914 to provide heating to the periodic structure 905 and the gas. The gas concentrator 900 may be configured as a trickle-bed reactor designed for co-current or counter current flow of the first gas and the heat transfer fluid simultaneously. Although depicted as being horizontal, the flow path 914 may be vertical. Some embodiments may include separate inlets or separate outlets for the gas and the heat transfer fluid.

Figure 10:
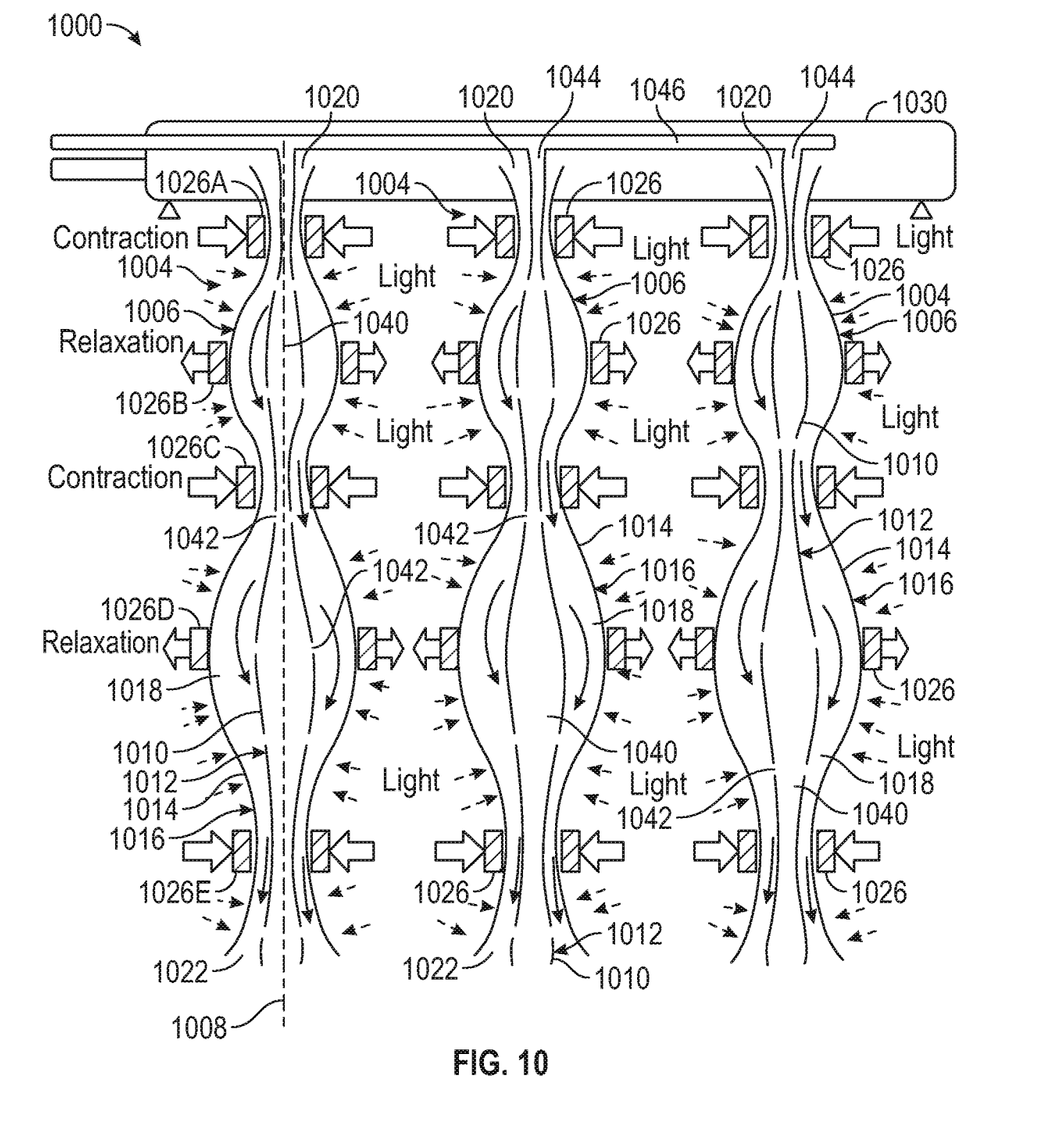
FIG. 10 illustrates a system for growing algae, according to one or more embodiments of the present disclosure.

FIG. 10 illustrates an example system 1000 for growing algae, according to one or more additional embodiments of the present disclosure. The system 1000 may be characterized as a photobioreactor system operable for the cultivation and growth of algae. In at least one embodiment, the system 1000 may be used as the PBR 104 in the system 100 of FIG. 1.

The system 1000 includes one or more photobioreactors (PBR) 1004. Each PBR 1004 includes a tubular structure 1006 extending along a longitudinal axis 1008 and having an inner sleeve 1010 defining an inner surface 1012 and an outer sleeve 1014 defining an outer surface 1016. Each PBR 1004 further includes an annular space 1018 defined between the inner and outer surfaces 1012, 1016, and an inlet 1020 to allow an algae slurry to enter the annular space 1018 and an exit 1022 to allow the algae slurry to be removed. The outer surface 1016 is transparent to at least some wavelengths of light useful for growing algae within the algae slurry, which may include water, algae, nutrients, and dissolved gases. The PBR 1004 further includes one or more mechanisms 1026 to produce movement of the outer surface 1016 and the outer sleeve 1014. In some embodiments, operation of the mechanisms 1026 may produce peristaltic motion in the tubular structures 1006 to promote the axial movement of the algae slurry through annular space 1018.

The system 1000 is shown with three PBRs 1004 positioned adjacent and aligned generally parallel to each other. Other embodiments may include more or fewer PBRs 1004. As illustrated, the PBRs 1004 may be supported by and may hang vertically from a support structure 1030 that may define or otherwise operate as an inlet manifold fluidically coupled to each inlet 1020 for the annular spaces 1018. The PBRs 1004 are arranged to allow ambient light to penetrate portions of the outer surface 1016 of each PBR 1004 to provide energy for the algae to grow. Other arrangements and various light sources are possible, without departing from the scope of the disclosure.

The outer surface 1016 and the inner surface 1012 may be periodic, as is depicted in FIG. 10. Alternatively, the outer sleeve 1014 and its outer surface 1016 or the inner sleeve 1010 and its inner surface 1012 may be cylindrical in shape and exhibit a constant diameter between the inlet 1020 and the outlet 1022. In such embodiments, the mechanisms 1026 may induce a temporary periodic shape to the outer sleeve 1014 and its outer surface 1016.

The inner sleeve 1010 defines an inner passageway 1040 and one or more apertures 1042 are provided in the inner sleeve to facilitate fluid communication between the inner passageway 1040 and the annular space 1018. The inner passageway 1040 includes an inlet 1044 to receive the gas, which, preferably includes $CO_2$. The gas provided to the inner passageway 1040 may come from any suitable source, including atmospheric air, flue gas/exhaust streams from a combustion process, or a storage location including tanks or geological formations, as examples. The system 1000 includes a gas manifold 1046 fluidically coupled to each of the inner passageways 1040. In some embodiments, the gas manifold 1046 may be integrated with the support structure 1030. In some embodiments, a gas concentrator (not shown) may be fluidly coupled to the gas manifold 1046 to provide the gas to the inner passageway 1040 and ultimately to the annular space 1018. The gas concentrator may be of a conventional design or may be any of the gas concentrators disclosed herein.

FIG. 10 shows a plurality of mechanisms 1026, axially spaced apart along the outer surface 1016 of each PBR 1004. In some embodiments, the mechanisms 1026 may extend circumferentially around the outer sleeve 1014 or its outer surface 1016 and constrict radially or circumferentially. In some embodiments, one or more of the mechanisms 1026 may include opposing plates that move linearly to compress or to relax a tubular structure 1006.

The individual mechanisms 1026 of the far-left PBR 1004 are distinguished by a letter designator, e.g., A, B, C, etc. In this example, a first mechanism 1026A is positioned at a first axial location along the tubular structure 1006 and configured to produce a first periodic cycle of contractions and expansions. A second mechanism 1026B is positioned at a second axial location along the tubular structure 1006 and configured to produce a second periodic cycle of contractions and expansions. A third mechanism 1026C is positioned at a third axial location along the tubular structure 1006 and configured to produce a third periodic cycle of contractions and expansions. Fourth and fifth mechanisms 1026D,E are similarly positioned and configured for operation. Some embodiments may have more or fewer than five mechanisms to induce motion in the tubular structure 1006. In some examples, the second periodic cycle of the contractions and expansions is out-of-phase with the first periodic cycle of the contractions and expansions. Also, the third periodic cycle of the contractions and expansions is out-of-phase with the second periodic cycle of the contractions and expansions. In some examples, the out-of-phase cycles of the contractions and expansions (e.g., any two of the mentioned periodic cycles or the first, second, and third periodic cycles working together) cause peristaltic motion in the outer sleeve 1014 of the tubular structure 1006.

Applicable to any of the PBRs 1004, algae may grow in the slurry within the annular space 1018, on the inner surface 1012, on the outer sleeve 1014, or in a combination of these locations. The motion of the outer sleeve 1014 induced by the mechanisms 1026, e.g., peristaltic motion, may cause or aid axial movement of the algae slurry through the annular space 1018 from the inlet 1020 to the exit 1022 or may act to loosen or remove algae that may be growing on the inner surface 1012 or on the outer sleeve 1014 to allow algae to be harvested. FIG. 10 includes arrows indicating radially-directed contractions and expansions of the mechanisms 1026 and the outer sleeve 1014 during a moment in time. In some embodiments, the mechanisms 1026 are configured to produce axially-directed movements in addition to or in placed of the radially-directed contractions and expansions. The operation of any PBR 1004 or the system 1000, including the movements of mechanisms 1026, may be governed by a controller, such as the control system 114 of FIG. 1.

EMBODIMENTS LISTING

The present disclosure provides, among others, the following embodiments, each of which may be considered as alternatively including any alternate embodiments.

Clause 1. A system for growing algae that includes a gas concentrator configured to receive a first gas containing CO2 at a first concentration and discharge a second gas containing CO2 at a second concentration higher than the first concentration, a photobioreactor containing algae in an algae slurry and fluidically coupled to the gas concentrator to receive the second gas, and a recycling line extending from a gas outlet on the photobioreactor to remove a third gas from the photobioreactor for future use in the photobioreactor.

Clause 2. The system of Clause 1, wherein the system further comprises a control system configured to direct the third gas from the photobioreactor through the recycling line.

Clause 3. The system of Clause 2, further comprising a transfer line fluidically coupling the gas concentrator and the photobioreactor, and a gas storage tank fluidically coupled to the recycling line to collect the third gas, wherein the recycling line is fluidically coupled to an inlet of the gas concentrator and to the transfer line, and wherein the control system is further configured to direct the third gas to at least one of the inlet of the gas concentrator, the transfer line, and the gas storage tank.

Clause 4. The system of any of the preceding Clauses, wherein the gas concentrator operates using a process selected from the group consisting of pressure swing adsorption, vacuum swing adsorption, voltage swing adsorption, temperature swing adsorption, displacement desorption, and any combination thereof.

Clause 5. The system of any of the preceding Clauses, wherein the gas concentrator is a first gas concentrator and the system further comprises a plurality of gas concentrators in fluid communication with the photobioreactor.

Clause 6. The system of Clause 5, wherein the photobioreactor is a pond and the plurality of gas concentrators are spaced apart along one or more islands extending across a portion of the pond.

Clause 7. The system of any of the preceding Clauses, wherein the gas concentrator further comprises a periodic surface and an adsorbent material disposed adjacent or on the periodic surface, wherein the adsorbent material absorbs $CO_2$ from the first gas.

Clause 8. The system of any of the preceding Clauses, wherein the gas concentrator comprises a feature selected from a group consisting of metal organic framework (MOF), amine-appended MOF with a Type V isotherm for $CO_2$, an amine appended MOF with a Type 1 isotherm for $CO_2$, a metal impregnated microporous silicate, metal impregnated alkalized alumina, mixed-metal oxides, hydrotalcites, treated activated carbons including metal doped carbons, and any combination thereof.

Clause 9. A method for growing algae includes receiving a first gas containing $CO_2$ of a first concentration into a gas concentrator, discharging a second gas containing $CO_2$ of a higher, second concentration from the gas concentrator, delivering the second gas to a photobioreactor containing algae in an algae slurry, wherein the gas concentrator is fluidically coupled to the photobioreactor, discharging a third gas from the photobioreactor, and recycling at least a portion of the third gas back to the photobioreactor.

Clause 10. The method of Clause 9, further comprising combining at least a portion of the third gas with the second gas prior to delivering the second gas to the photobioreactor.

Clause 11. The method of Clause 10, further comprising delivering a portion of the third gas to the gas concentrator, wherein the third gas contains $CO_2$ released from the algae.

Clause 12. The method of any of Clauses 9 to 11, further comprising obtaining the second gas at the higher, second concentration with the gas concentrator using a process selected from the group consisting of pressure swing adsorption, vacuum swing adsorption, voltage swing adsorption, temperature swing adsorption, displacement desorption, and any combination thereof.

Clause 13. The method of any of Clauses 9 to 12, wherein the gas concentrator includes a first flow path comprising a periodic surface, the method further comprising receiving the first gas into the first flow path, obtaining the second gas from the first flow path, and passing a heat transfer liquid through the gas concentrator to provide cooling.

Clause 14. The method of Clause 13, wherein passing the heat transfer liquid through the gas concentrator comprises passing the heat transfer liquid through the first flow path.

Clause 15. The method of Clause 13, further comprising producing contractions and expansions on the periodic surface as the first gas flows through the first flow path.

Clause 16. The method of Clause 13, further comprising producing a first periodic cycle of contractions and expansions on the periodic surface at a first location, and producing a second periodic cycle of contractions and expansions on the periodic surface at a second location spaced apart from the first location, wherein the second periodic cycle of periodic contractions and expansions are out-of-phase with the first periodic cycle of contractions and expansions.

Clause 17. The method of Clause 16, further comprising causing peristaltic motion in the periodic surface.

Clause 18. A gas concentrator includes a periodic structure comprising a first, periodic surface and a second surface, an adsorbent material disposed adjacent or on the first, periodic surface to absorb $CO_2$ from a mixture of gases, a first flow path that is at least partially defined by the first, periodic surface and the adsorbent material, and a second flow path that includes the second surface.

Clause 19. The gas concentrator of Clause 18, wherein the adsorbent material is attached to the first, periodic surface.

Clause 20. The gas concentrator of Clause 19, wherein the adsorbent material coats the first, periodic surface.

Clause 21. The gas concentrator of any of Clauses 18 to 20, wherein the second flow path is disposed inside the periodic structure and is fluidically separated from the first flow path.

Clause 22. The gas concentrator of any of Clauses 18 to 21, wherein the periodic structure is a first periodic structure and the gas concentrator includes a plurality of periodic structures, and wherein the first flow path includes the first, periodic surfaces of the plurality of periodic structures, and the second flow path includes the second surfaces of the plurality of periodic structures.

Clause 23. The gas concentrator of any of Clauses 18 to 22, wherein the adsorbent material comprises a first portion of granules or monoliths disposed adjacent the first, periodic surface, and a second portion of granules or monoliths disposed adjacent the second surface.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms used herein, including the claims, have their plain, ordinary meaning unless otherwise explicitly and clearly defined by the patentee. Moreover, the indefinite articles "a" or "an," as used herein, including the claims, are defined herein to mean one or more than one of the element that it introduces.

The term "or" as used in a phrase such as "A or B" herein is intended to include alternatively of any of the following: "A" alone, "B" alone, and, where feasible, "A and B." Ordinal numbers such as first, second, third, etc. do not indicate a quantity but are used for naming and reference purposes. In addition, ordinal numbers used in the claims in reference to a component or feature may differ from the ordinal numbers used in the written description for the corresponding component or feature. For example, a "second object" in a claim might be described as a "third object" or may be described without an ordinal number in the written description.

As used herein, including the claims, the term "line" for fluid communication may include any of the following pipe, piping, tubing, hose, fittings, valves, gauges, check valves, flow meters, filters, and the like.

Unless otherwise indicated, all numbers expressing quantities of ingredients, properties such as length, volume, mass, molecular weight, operating conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

For the sake of clarity, not all features of a physical embodiment are described or shown in this application. It is understood that in the development of a physical embodiment incorporating the embodiments of the present disclosure, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for those of ordinary skill in the art and having benefit of this disclosure.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The illustrative embodiments disclosed herein suitably may be implemented in the absence of any element that is not specifically disclosed herein and/or any alternative element disclosed herein. While components, compositions, and methods are described in terms of "comprising," "containing," or "including" various components or steps, the components, compositions, and methods can also "consist essentially of" or "consist of" the various components and steps. For the methods herein, the order of various process steps may be rearranged in some embodiments and yet remain within the scope of the disclosure, including the claims.

The invention claimed is:

1. A system for growing algae, comprising:
a gas concentrator configured to receive a first gas containing $CO_2$ at a first concentration and discharge a second gas containing $CO_2$ at a second concentration higher than the first concentration, wherein the gas concentrator comprises a periodic structure comprising at least a first periodic surface, and an adsorbent material disposed adjacent or on the periodic surface and the adsorbent material absorbs $CO_2$ from the first gas;
a photobioreactor containing algae in an algae slurry and fluidically coupled to the gas concentrator to receive the second gas; and
a recycling line extending from a gas outlet on the photobioreactor to remove a third gas from the photobioreactor for future use in the photobioreactor,
wherein the periodic structure moves to induce peristaltic motion thereof.

2. The system of claim 1, wherein the system further comprises a control system configured to direct the third gas from the photobioreactor through the recycling line.

3. The system of claim 2, further comprising:
a transfer line fluidically coupling the gas concentrator and the photobioreactor; and
a gas storage tank fluidically coupled to the recycling line to collect the third gas, wherein the recycling line is fluidically coupled to an inlet of the gas concentrator and to the transfer line, and
wherein the control system is further configured to direct the third gas to at least one of the inlet of the gas concentrator, the transfer line, and the gas storage tank.

4. The system of claim 1, wherein the gas concentrator operates using a process selected from the group consisting of pressure swing adsorption, vacuum swing adsorption, voltage swing adsorption, temperature swing adsorption, displacement desorption, and any combination thereof.

5. The system of claim 1, wherein the gas concentrator is a first gas concentrator and the system further comprises a plurality of gas concentrators in fluid communication with the photobioreactor.

6. The system of claim 5, wherein the photobioreactor is a pond and the plurality of gas concentrators are spaced apart along one or more islands extending across a portion of the pond.

7. The system of claim 1, wherein the absorbent material is selected from a group consisting of metal organic framework (MOF), amine-appended MOF with a Type V isotherm for $CO_2$, an amine appended MOF with a Type 1 isotherm for $CO_2$, a metal impregnated microporous silicate, metal impregnated alkalized alumina, mixed-metal oxides, hydrotalcites, treated activated carbons including metal doped carbons, and any combination thereof.

* * * * *